US012805866B2

(12) United States Patent
Bear

(10) Patent No.: US 12,805,866 B2
(45) Date of Patent: Nov. 24, 2026

(54) IN-DEVICE DISPLACEMENT SENSING

(71) Applicant: Cilag GmbH International, Zug (CH)

(72) Inventor: Brian Bear, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/627,029

(22) Filed: Apr. 4, 2024

(65) Prior Publication Data

US 2025/0312039 A1 Oct. 9, 2025

(51) Int. Cl.

*A61B 17/072* (2006.01)
*A61B 17/00* (2006.01)
*A61B 17/068* (2006.01)
*A61B 90/00* (2016.01)

(52) U.S. Cl.

CPC .. *A61B 17/07207* (2013.01); *A61B 17/00234* (2013.01); *A61B 17/0686* (2013.01); *A61B 90/06* (2016.02); *A61B 90/08* (2016.02); *A61B 2017/00075* (2013.01); *A61B 2017/00296* (2013.01); *A61B 2017/00477* (2013.01); *A61B 2017/00867* (2013.01); *A61B 2017/07257* (2013.01); *A61B 2017/07271* (2013.01); *A61B 2017/07278* (2013.01); *A61B 2017/07285* (2013.01); *A61B 2090/067* (2016.02); *A61B 2090/0811* (2016.02)

(58) Field of Classification Search

CPC ........ A61B 17/07207; A61B 17/00234; A61B 90/06; A61B 90/08; A61B 2090/0811; A61B 2090/067
USPC ........................................... 227/175.1–181.1
See application file for complete search history.

(56) References Cited

U.S. PATENT DOCUMENTS 7,810,692 B2 * 10/2010 Hall ................. A61B 17/07207 227/176.1
8,210,411 B2 7/2012 Yates et al.
9,186,142 B2 11/2015 Fanelli et al.
9,517,065 B2 12/2016 Simms et al.
9,622,746 B2 4/2017 Simms et al.
9,717,497 B2 8/2017 Zerkle et al.
9,795,379 B2 10/2017 Leimbach et al.
9,808,248 B2 11/2017 Hoffman
9,839,421 B2 12/2017 Zerkle et al.
10,092,292 B2 10/2018 Boudreaux et al.
11,304,697 B2 4/2022 Fanelli et al.
11,317,912 B2 5/2022 Jenkins et al.
11,439,391 B2 9/2022 Bruns et al.
2012/0116267 A1 * 5/2012 Kimball ................. G16H 20/40 606/1
2014/0025067 A1 * 1/2014 Kerr ................... A61B 18/1206 606/41
2014/0039519 A1 * 2/2014 Inoue ..................... A61B 34/37 901/8
2016/0015255 A1 * 1/2016 Dejima .............. A61B 17/3423 600/106

(Continued)

*Primary Examiner* — Linda J. Hodge
(74) *Attorney, Agent, or Firm* — Lempia Summerfield Katz LLC

(57) ABSTRACT

A system including a direct mechanical connection to a moveable stapler component within a surgical stapler. The system includes a sensor that detects a position of a mechanical connector that is attached to the moveable stapler component, where the direct measurement of the moveable stapler component is used to determine the position, pose, displacement, stability, or orientation of the moveable stapler component and/or surgical stapler.

16 Claims, 14 Drawing Sheets

(56) References Cited

U.S. PATENT DOCUMENTS

| | | | | |
|---|---|---|---|---|
| 2016/0174977 | A1* | 6/2016 | Lytle, IV | A61B 17/068<br>227/180.1 |
| 2017/0105731 | A1* | 4/2017 | Scheib | A61B 17/105 |
| 2018/0146962 | A1* | 5/2018 | Kostrzewski | A61B 17/07207 |
| 2018/0250004 | A1* | 9/2018 | Williams | A61B 17/072 |
| 2021/0030490 | A1* | 2/2021 | Miyahara | G01D 5/12 |
| 2021/0386449 | A1* | 12/2021 | Bueno | A61B 17/320016 |

* cited by examiner

IN-DEVICE DISPLACEMENT SENSING

BACKGROUND

In some settings, laparoscopic or endoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

The pose (i.e., pitch and yaw) and anvil position (i.e., jaw opening or angle) of the end effectors is an important piece of information when using the endoscopic surgical instruments. Electronically detecting the end effector pose and anvil position may be difficult due to challenges in placing and reading sensors located in the end effectors, e.g., near the components to be measured.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
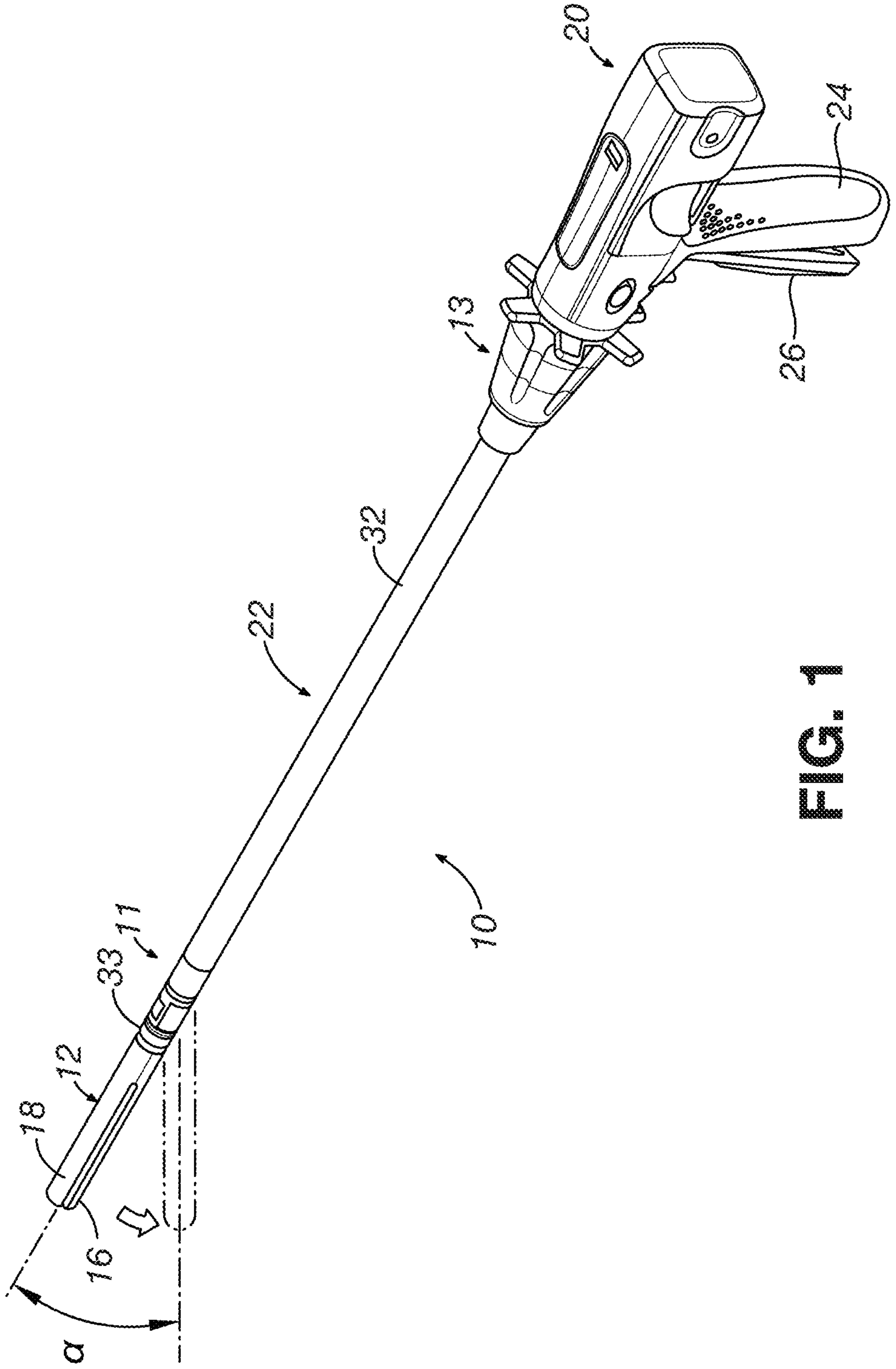
FIG. 1 depicts a perspective view of an example of an articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those having ordinary skill in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures.

As used herein in connection with various examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. Illustrative Surgical Stapler

FIGS. 1-7 depict an example of a surgical stapling and severing instrument 10 that is sized for insertion through a trocar cannula or an incision (e.g., thoracotomy, etc.) to a surgical site in a patient for performing a surgical procedure. Instrument 10 of the present example includes a handle portion 20 connected to a shaft 22, which distally terminates in an articulation joint 11, which is further coupled with an end effector 12. Once articulation joint 11 and end effector 12 are inserted through the cannula passageway of a trocar, articulation joint 11 may be remotely articulated, as depicted in phantom in FIG. 1, by an articulation control 13, such that end effector 12 may be deflected from the longitudinal axis (LA) of shaft 22 at a desired angle (α). End effector 12 of the present example includes a lower jaw 16 (also referred to herein as a cartridge jaw) that includes a staple cartridge 37, and an upper jaw in the form of a pivotable anvil jaw 18.

Unless otherwise described, the term "pivot" (and variations thereof) as used herein encompasses but is not necessarily limited to pivotal movement about a fixed axis. For instance, in some versions, anvil jaw 18 may pivot about an axis that is defined by a pin (or similar feature) that slidably translates along an elongate slot or channel as anvil jaw 18 moves toward lower jaw 16. Such translation may occur before, during, or after the pivotal motion. It should therefore be understood that such combinations of pivotal and translational movement are encompassed by the term "pivot" and variations thereof as used herein. The term "anvil position" as used herein encompasses but is not necessarily limited to the position of the anvil (or anvil/upper jaw) with respect to the staple cartridge channel (or cartridge/lower jaw), or in other words, the jaw opening position, also called "aperture" or jaw angle. The term "pose" (and variations thereof) as used herein encompasses but is not necessarily limited to the pitch and yaw of the end effector or device. In other words, the term "pose" refers to the angular position of the end effector or device around a horizontal and vertical axis relative to the device shaft 22. Different devices may have only one angle adjustment (pitch or yaw), two angle adjustments (pitch+yaw), or a third axis adjustment such as the roll or tip roll. The term "stability" of the device is used herein to refer to detecting any change in position or pose of the device.

Handle portion 20 includes a pistol grip 24 and a closure trigger 26. Closure trigger 26 is pivotable toward pistol grip 24 to cause clamping, or closing, of anvil jaw 18 toward lower jaw 16 of end effector 12. Such closing of anvil jaw 18 is provided through a closure tube 32 and a closure ring 33, which both longitudinally translate relative to handle portion 20 in response to pivoting of closure trigger 26 relative to pistol grip 24. Closure tube 32 extends along the length of shaft 22; and closure ring 33 is positioned distal to articulation joint 11. Articulation joint 11 is operable to communicate/transmit longitudinal movement from closure tube 32 to closure ring 33. Other closure systems may be used, such as using a firing member, such as the cutting edge 48 of firing beam 14, for closure rather than a separate closure mechanism.

Figure 2:
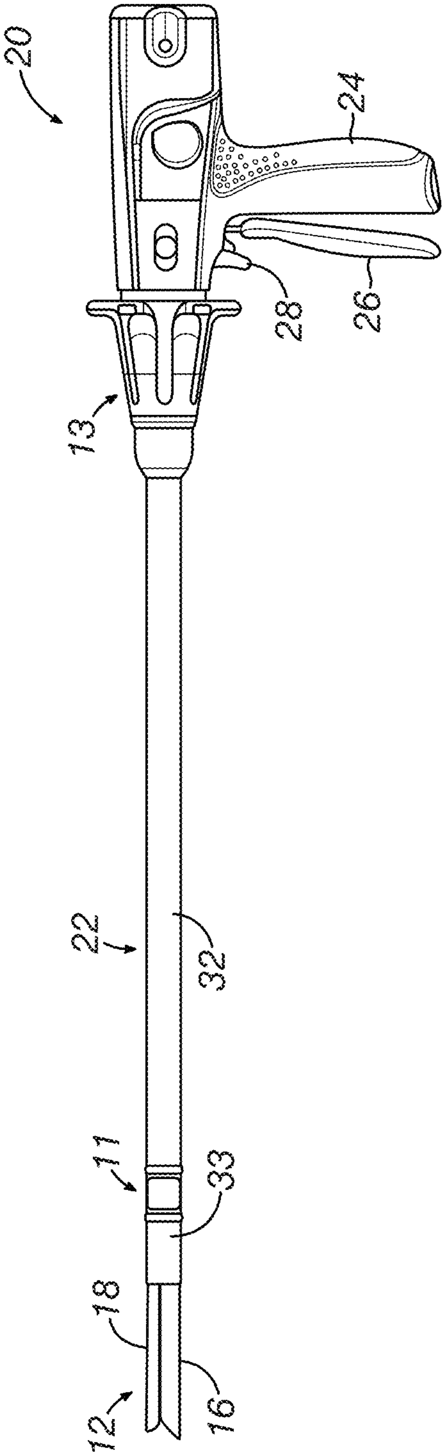
FIG. 2 depicts a side view of the instrument of FIG. 1.

As shown in FIG. 2, handle portion 20 also includes a firing trigger 28. An elongate member (not shown) longitudinally extends through shaft 22 and communicates a longitudinal firing motion from handle portion 20 to a firing beam 14 in response to actuation of firing trigger 28. This distal translation of firing beam 14 causes the stapling and severing of clamped tissue in end effector 12, as will be described in greater detail below.

As shown in FIGS. 3-6, end effector 12 employs a firing beam 14 that includes a transversely oriented upper pin 38, a firing beam cap 44, a transversely oriented middle pin 46, and a distally presented cutting edge 48. Upper pin 38 is positioned and translatable within a longitudinal anvil slot 42 of anvil jaw 18. Firing beam cap 44 slidably engages a lower surface of lower jaw 16 by having firing beam 14 extend through lower jaw slot 45 (shown in FIG. 4B) that is formed through lower jaw 16. Middle pin 46 slidingly engages a top surface of lower jaw 16, cooperating with firing beam cap 44.

Figure 3:
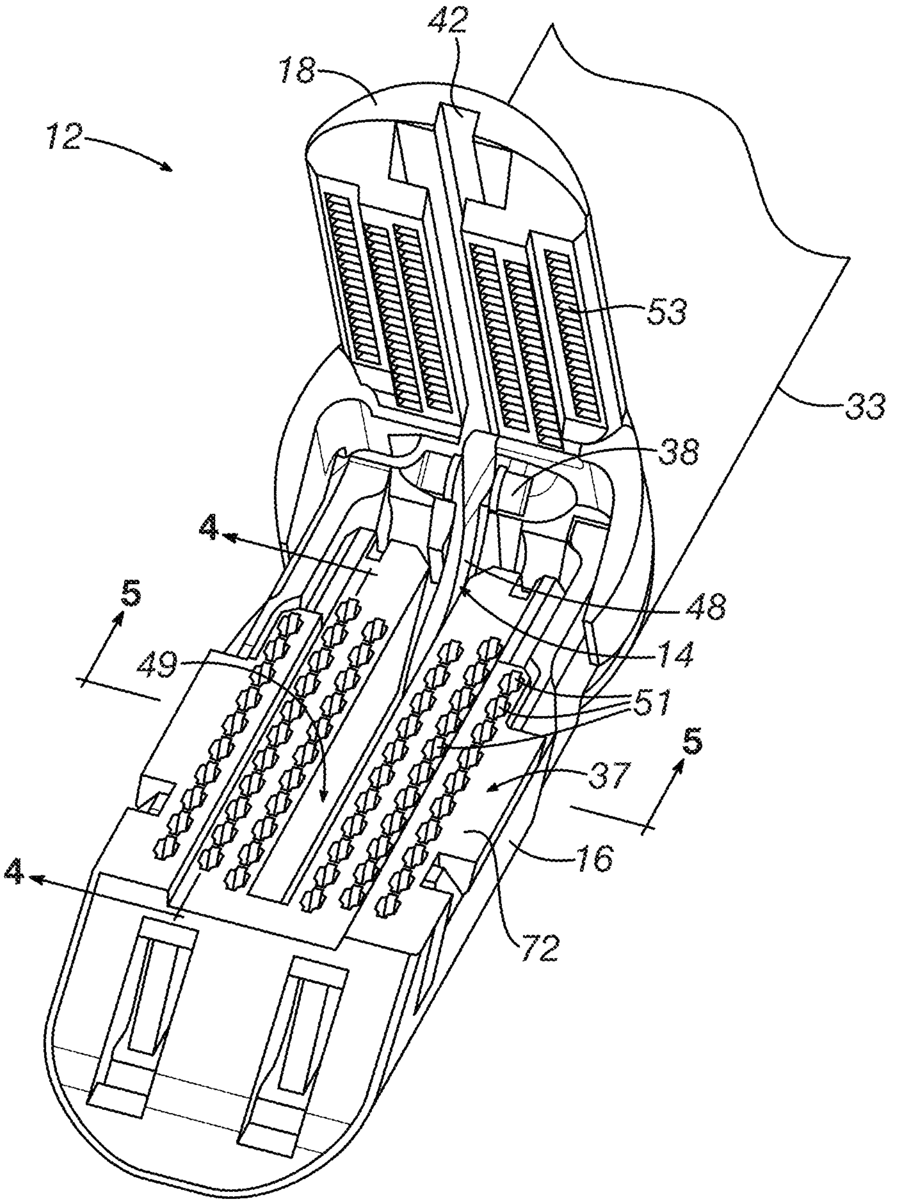
FIG. 3 depicts a perspective view of an opened end effector of the instrument of FIG. 1.
Figure 4A:
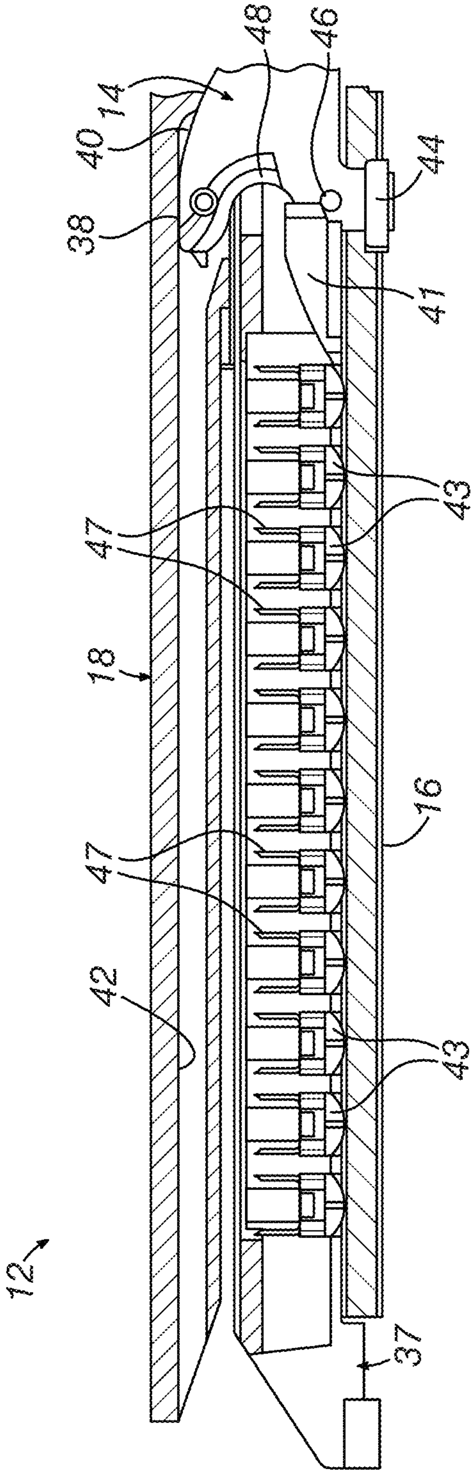
FIG. 4A depicts a side cross-sectional view of the end effector of FIG. 3, taken along line 4-4 of FIG. 3, with the firing beam in a proximal position.
Figure 4B:
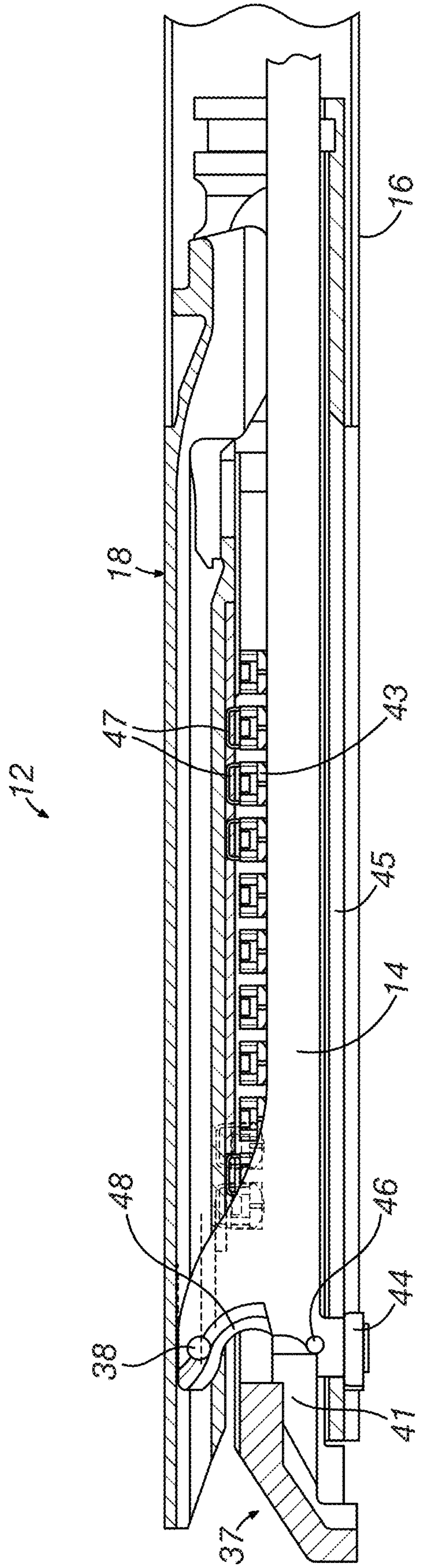
FIG. 4B depicts a side cross-sectional view of the end effector of FIG. 3, taken along line 4-4 of FIG. 3, with the firing beam in a distal position.
Figure 5:
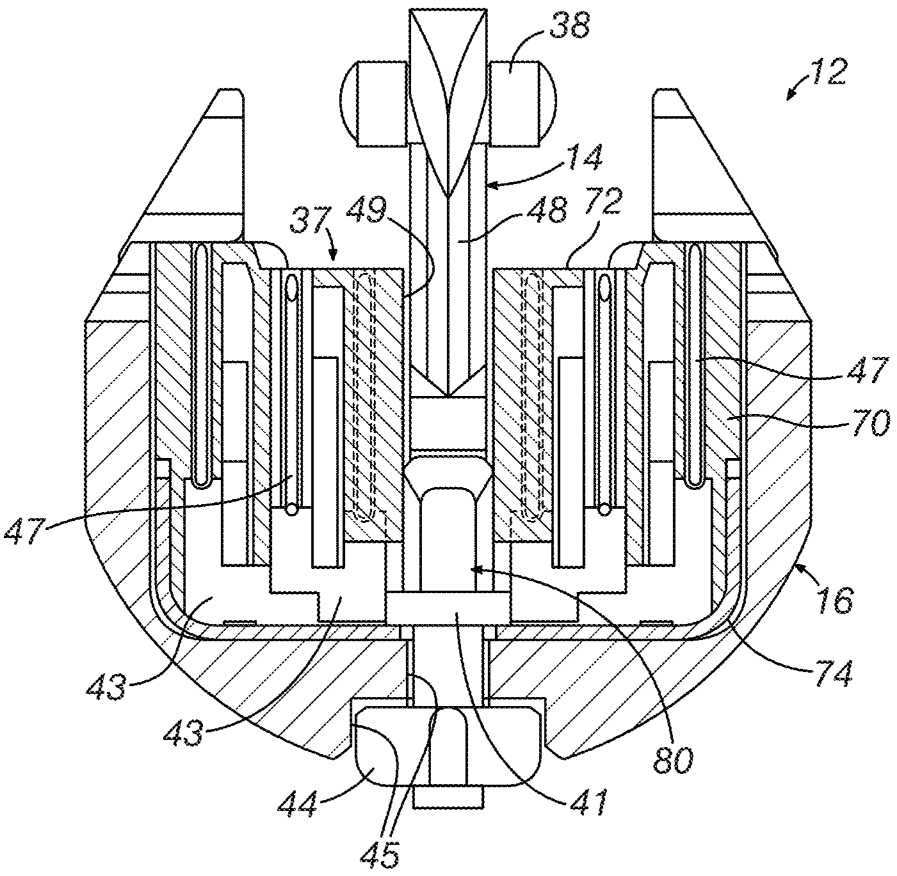
FIG. 5 depicts an end cross-sectional view of the end effector of FIG. 3, taken along line 5-5 of FIG. 3.
Figure 6:
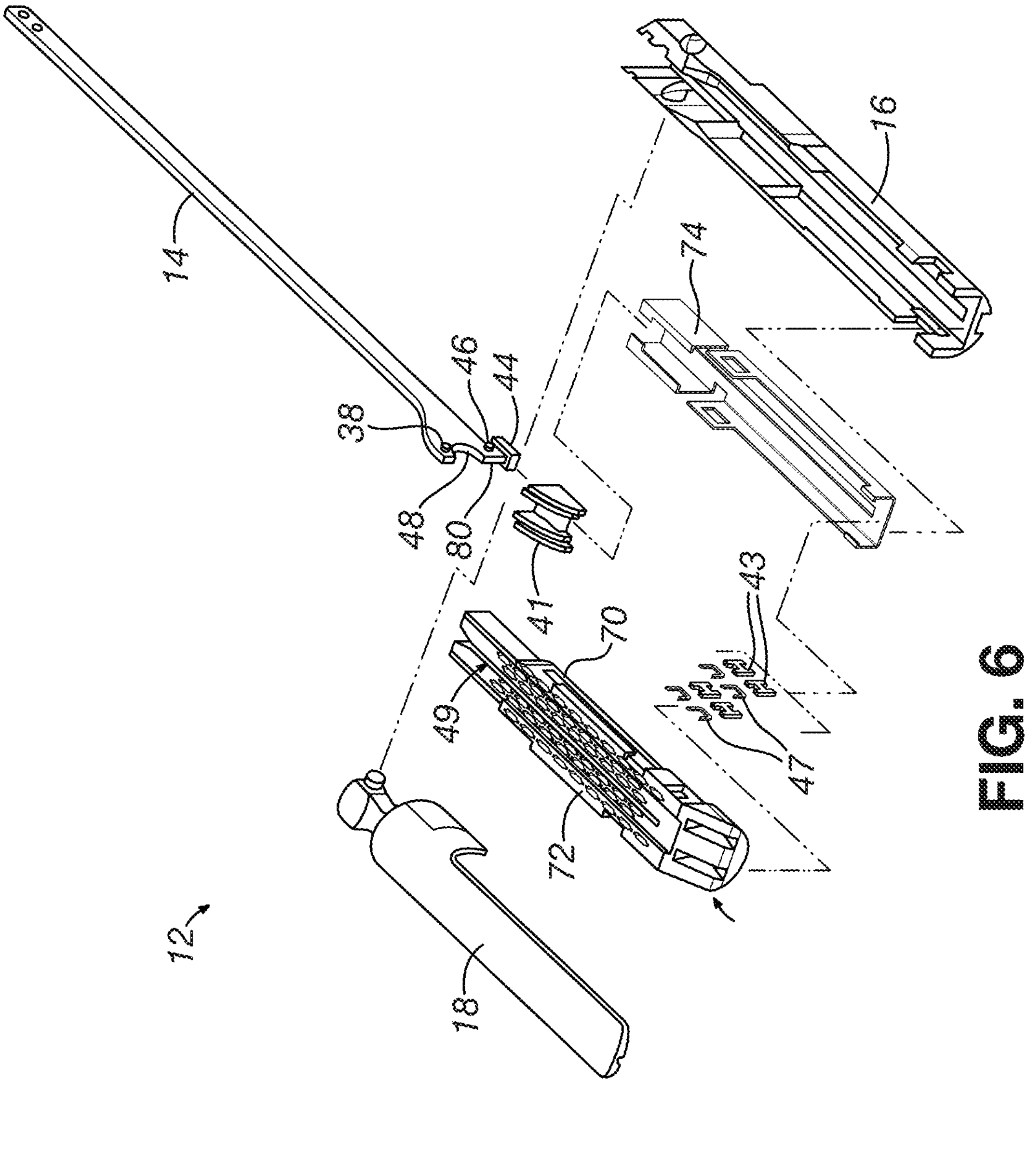
FIG. 6 depicts an exploded perspective view of the end effector of FIG. 3.

FIG. 3 shows firing beam 14 of the present example proximally positioned and anvil jaw 18 pivoted to an open configuration; allowing an unspent staple cartridge 37 to be removably installed into a channel of lower jaw 16. As best seen in FIGS. 5-6, staple cartridge 37 of the present example includes a cartridge body 70, which presents an upper deck 72 and is coupled with a lower cartridge tray 74. As best seen in FIG. 3, a vertical slot 49 extends longitudinally through a portion of staple cartridge body 70. As also best seen in FIG. 3, three rows of staple apertures 51 are formed through upper deck 72 on each lateral side of vertical slot 49. As shown in FIGS. 4A-6, a wedge sled 41 and a plurality of staple drivers 43 are captured between cartridge body 70 and tray 74, with wedge sled 41 being located proximal to staple drivers 43. Wedge sled 41 is movable longitudinally within staple cartridge 37; while staple drivers 43 are movable vertically within staple cartridge 37. Staples 47 are also positioned within cartridge body 70, above corresponding staple drivers 43. Each staple 47 is driven vertically within cartridge body 70 by a staple driver 43 to drive staple 47 out through an associated staple aperture 51. As best seen in FIGS. 4A-4B and 6, wedge sled 41 presents inclined cam surfaces that urge staple drivers 43 upwardly as wedge sled 41 is driven distally through staple cartridge 37.

With end effector 12 closed, as depicted in FIGS. 4A-4B by distally advancing closure tube 32 and closure ring 33, a firing member in the form of firing beam 14 is then advanced distally into engagement with anvil jaw 18 by having upper pin 38 enter longitudinal anvil slot 42. A pusher block 80 (shown in FIG. 5) located at distal end of firing beam 14 pushes wedge sled 41 distally as firing beam 14 is advanced distally through staple cartridge 37 when firing trigger 28 is actuated. During such firing, cutting edge 48 of firing beam 14 enters vertical slot 49 of staple cartridge 37, severing tissue clamped between staple cartridge 37 and anvil jaw 18.

As shown in FIGS. 4A-4B, middle pin 46 and pusher block 80 together actuate staple cartridge 37 by entering into vertical slot 49 within staple cartridge 37, driving wedge sled 41 into upward camming contact with staple drivers 43, which in turn drives staples 47 out through staple apertures 51 and into forming contact with staple forming pockets 53 (shown in FIG. 3) on inner surface of anvil jaw 18. FIG. 4B depicts firing beam 14 fully distally translated after completing severing and stapling of tissue. Staple forming pockets 53 are intentionally omitted from the view in FIGS. 4A-4B but are shown in FIG. 3. Anvil jaw 18 is intentionally omitted from the view in FIG. 5.

Figure 7:
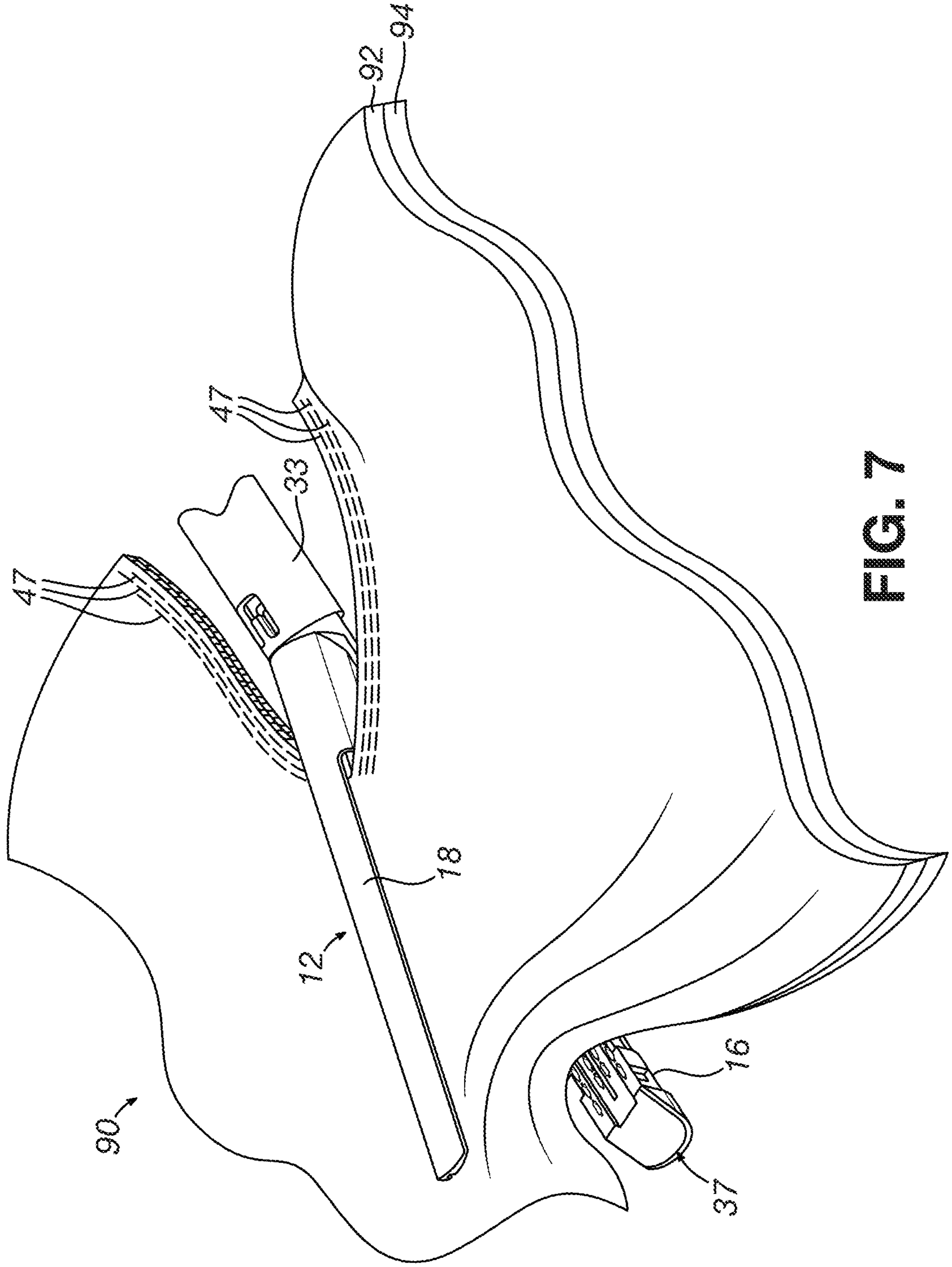
FIG. 7 depicts a perspective view of the end effector of FIG. 3, positioned at tissue and having been actuated once in the tissue.

FIG. 7 shows end effector 12 having been actuated through a single firing stroke through tissue 90. Cutting edge 48 (obscured in FIG. 7) has cut through tissue 90, while staple drivers 43 have driven three alternating rows of staples 47 through tissue 90 on each side of the cut line produced by cutting edge 48. After the first firing stroke is complete, end effector 12 is withdrawn from the patient, spent staple cartridge 37 is replaced with a new staple cartridge 37, and end effector 12 is then again inserted into the patient to reach the stapling site for further cutting and stapling. This process may be repeated until the desired quantity and pattern of firing strokes across the tissue 90 has been completed.

Instrument 10 may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. In-Device Displacement Sensing

The features of the present disclosure seek to enable a clinician to quickly and precisely identify a pose (i.e., pitch and yaw) and anvil position (i.e., jaw opening or angle) of an end effector prior to or during a surgical procedure.

In at least one form, a surgical instrument may include a handle, a shaft 22 comprising a proximal shaft portion coupled to the handle and a distal shaft portion, and an articulation joint 11 connected to the distal shaft portion. The surgical instrument may further include an end effector 12 including a proximal end coupled to the articulation joint 11, a distal end, a first jaw member, a second jaw member, wherein one of the first jaw member and the second jaw member is movable relative to the other of the first jaw member and the second jaw member, for example where the first jaw member is a lower jaw 16 (also referred to herein as a cartridge jaw) that includes a staple cartridge 37, and the second jaw member is an upper jaw in the form of a pivotable anvil jaw 18. Alternative end effectors may be used that include different movable components.

In some instances, it may be desirable to determine a pose or position of components of the endoscopic device including the end effector 12. In an example, the pose or position may be used to determine if components of the end effector 12 have been deformed or otherwise not in a ground or factory calibrated position (i.e., an initial or known position before any movement or deformation). The pose or position of a component may be determined by identifying a starting pose or position of the component and then detecting subsequent movement or displacement. In addition, these components (articulation joint 11, first jaw member 16, second jaw member 18, etc.) may move relative to one another. Measuring the relative movement between components may allow for a determination of the stability or state of the end effector 12 and components included therein. Deploying sensors at the end effector 12 of an endoscopic device to measure the movement presents many technical challenges. When placed in the end effector 12, the sensors may be exposed to many hazards, both while in-use and in non-surgical handling (such as back-table preparation and shipping). Sensors that rely on a field effect (such as magnetism, Hall-effect, RF, etc.) may also suffer from range limits and non-linearity which must be corrected in subsequent signal-processing. To function, sensors may also be exposed or close to the external envelope of the device, making the sensors vulnerable to damage or interference. In addition, reading the mechanical displacement information from secondary or tertiary moving parts (such as articulation cables running through the shaft of the surgical instrument to control articulation of the end effector 12) leads to errors and assumptions, because these moving parts may be load-bearing and present accuracy issues as a measurement system (due to friction and compliance).

Embodiments described herein provide sensor(s) 110 located away from the distal end of the endoscopic device that are able to measure movement or displacement of components at the distal end of the endoscopic device, such as, for example, the lower jaw 16, pivotable anvil jaw 18, articulation joint 11 and the like. Movement of the components is measured by the sensors 110 using a direct mechanical connection to the components. The sensors 110 provide a digital, linear signal directly proportional to the desired mechanical characteristic, such as a device pose (pitch, yaw) or anvil position. By moving the sensors 110 away from the end effector 12 and into the shaft 22 and by providing dedicated mechanical connectors 120, embodiments avoid taking measurements off parts that are not directly connected to the desired quantity to be measured (such as articulation cables or bands) and further avoid making assumptions about the positional relationship.

In an example embodiment, the sensor 110 may be an electromagnetic encoder and is included within a shaft 22 of a surgical stapler device. The electromagnetic encoder detects a position of a scale 130 such as a magnet that is mechanically attached to a moveable stapler component, for example by a mechanical connector 120 such as a wire, tape, or filament that leads from the movable stapler component of an end effector 12 of the surgical stapler device to the scale 130 and sensor 110 that are located in the shaft 22. The direct measurement of the moveable stapler component may be used to verify the stability, pose, or position of the end effector 12 of the surgical stapler device.

In addition to a more accurate understanding of the position, orientation, or movement of the moveable stapler component or mechanical part, embodiments provide further benefits. The sensing electronics disclosed herein are housed inside the shaft 22 or handle of the device. The sensing electronics may thus be located in "safe" areas of the device where space is not at a premium and away from locations that risk physical damage. As the mechanical connector 120 is mechanical, there are no difficult passthroughs of electrical signals. This avoids routing electrical signals through tortuous mechanical paths into the distal tip of the end effector 12. In addition, the mechanical connector 120 (to the component-of-interest) may be provided by thin filaments or wires that are easily routed through the device and robust enough to retain function, even when damaged. Sensors 110 such as linear encoder read-heads may be miniaturized and provide several communication options such as single-wire digital, RS-422, quadrature, or analog. The scale 130 may also be specified for determining absolute measurement. The ability to determine an absolute position of the component allows for power-off of the device without losing the identity of the position of the component on power-on. This feature may eliminate the need to home or reset the component/end effector to a ground or home position.

Figure 8:
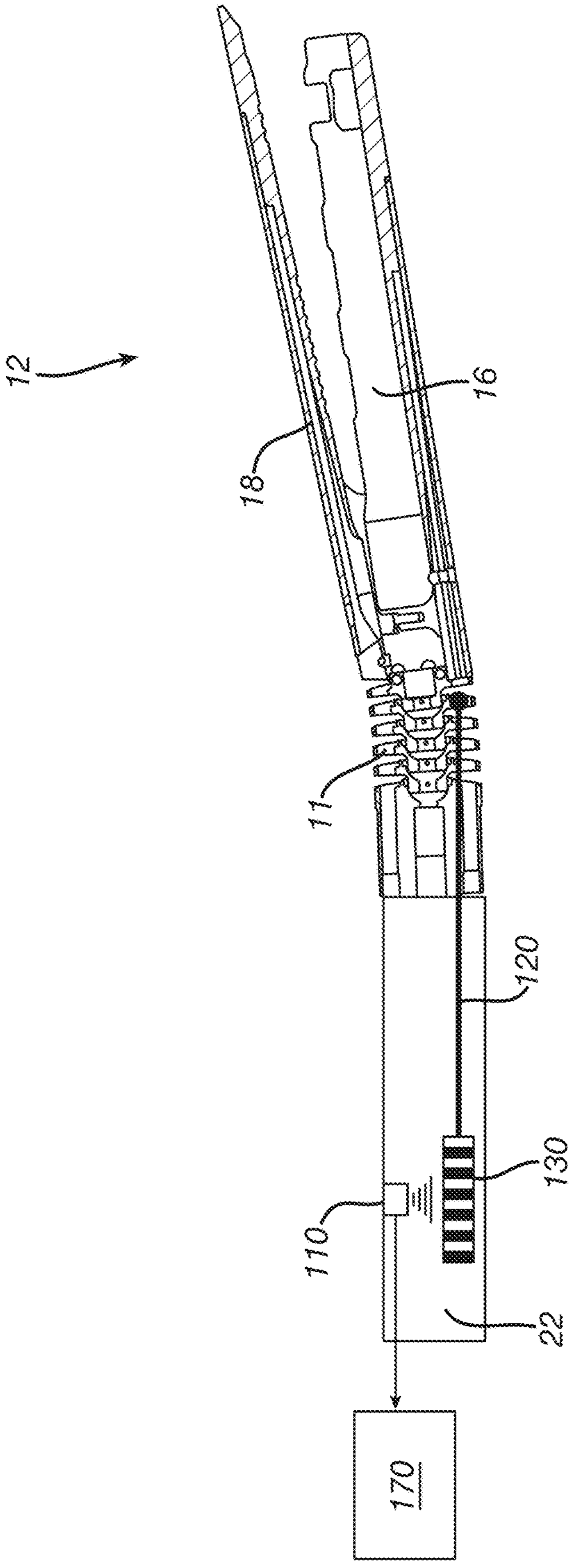
FIG. 8 depicts a side view of a system for detecting movement of a component of an end effector.

Referring now to the figures, FIG. 8 depicts an example of a system for detecting displacement of one or more mechanical parts. FIG. 8 includes a sensor 110, a mechanical coupling, linkage or connector 120 (for example, a wire), a scale 130 (e.g., a coded section of the connector 120), a shaft 22, an articulation joint 11, and an end effector 12. Not shown are other components such as a handle attached to a proximal end of the shaft 22. The shaft 22, which distally terminates in the articulation joint 11, is coupled with an end effector 12. In other words, the articulation joint 11 couples the end effector 12 to the shaft 22. The end effector 12 includes a lower jaw 16 (also referred to as a cartridge jaw) that includes a staple cartridge, and an upper jaw 18 in the form of a pivotable anvil jaw 18.

The sensor 110 is configured to sense, detect or read the scale 130 as the scale 130 slides past the sensor 110. The sensor 110 may be fixed or movable. When fixed, the sensor 110 measures the movement of the scale 130 as the scale 130 moves past, through or proximate to the sensor 110. When movable, the sensor 110 measures the relative movement of the scale 130 in relation to the sensor 110. The scale 130 is included with or physically connected to the movable component to be monitored using a mechanical connector 120. In application, as the movable component, such as an articulation joint 11, the lower jaw 16, or the upper jaw 18, moves or is displaced, the scale 130 also moves since the scale 130 is mechanically connected to the movable component. The sensor 110 measures the movement by reading the scale 130 as the scale 130 moves back and forth. In an embodiment, the optical, magnetic or mechanical indications induce the sensor 110 to generate a signal when an indicator passes by or through the sensor 110. Measuring the signals may provide an indication of the degree and rate/speed of movement. Pulse width/duration may be controlled by the size of each indication and the size need not be uniform. Using different size indications to create different pulse widths may be used to enable determination of directionality of movement, and when movement reaches a maximum or minimum range, etc. A device controller 170 or other processing unit, located in the handle (not shown) or shaft 22, analyzes the movement and provides feedback or information to an operator, such as, for example, a pose, position, or stability of the end effector 12. During operation, components of the end effector 12 may be moved, positioned, oriented, posed, and/or articulated. This movement, orientation, pose, and/or articulation may be detected and quantified by the system of FIG. 8.

In FIG. 8, a component of interest, e.g., movable component, is the articulation joint 11. Alternative components may be measured such as the jaw components (lower jaw 16, upper jaw 18), or other features or components of the end effector 12. The movable component may move a certain distance when the end effector 12 is articulated or used. The movement of the movable component is translated to the sensor 110 using a mechanical connector 120 attached to the movable component.

The mechanical connector 120 may be provided by a filament, wire, or other tendon-like object, for example a slender threadlike object or fiber. At a distal end of the mechanical connector 120, the mechanical connector 120 is attached to the movable component to be measured. The mechanical connector 120 may be attached, fastened, or joined to the movable component using any known type of attachment, fastener, or jointing process. In an example, the mechanical connector 120 is soldered to the movable component. The proximal end of the mechanical connector 120 includes, or is attached to, a coded section referred to as a scale 130 as described below. The proximal end of the mechanical connector 120 is not fixed but may move freely back and forth along the long axis of the shaft 22 (i.e., distally or proximally within the shaft 22). A housing, channel, and/or guide(s) may be provided that prevents lateral movement of the mechanical connector 120. In this regard, the housing, channel, and/or guide(s) may isolate the mechanical connector 120 from other moving components of the endoscopic device/shaft 22.

The mechanical connector 120 may be made of any material that provides or allows for translation of the movement of the distal end of the mechanical connector 120 (the movable component) to the proximal end of the mechanical connector 120 (the scale 130/coded section). In other words, when the proximal end of the mechanical connector 120 moves a certain distance, the distal end of the mechanical connector 120 moves a similar/same distance and vice versa. The material may have a level of stiffness or compliance so that the mechanical connector 120 does not stretch, fold, or deform longitudinally when the mechanical connector 120 moves back and forth due to the movement of the movable component. In an embodiment, the mechanical connector 120 is a thin filament made of a metal alloy such as steel or nitinol. The mechanical connector 120 may be a strip, strand, cable, link, and the like. The mechanical connector 120 may be, for example, a rigid cable or semi-rigid or semi-flexible wire.

The mechanical connector 120 is not fixed at one end (e.g., the proximal end) and thus is not under stress. The mechanical connector 120 is designed to be able to handle the movement of the movable component that the mechanical connector 120 is attached to and not any additional load. Thus, the mechanical connector 120 may include a small cross section, for example between 0.1 and 0.3 mm. In certain scenarios, the mechanical connector 120 may be straight from a distal end of the mechanical connector 120 attached to the movable component to a proximal end of the mechanical connector 120 that includes the scale 130. In other scenarios the mechanical connector 120 may be bent, curved, or otherwise not straight in order to avoid other components between the sensor 110 and the movable component. A guide, channel, or sheath may be used to guide the movable component through one or more curves or bends.

Figure 9A:
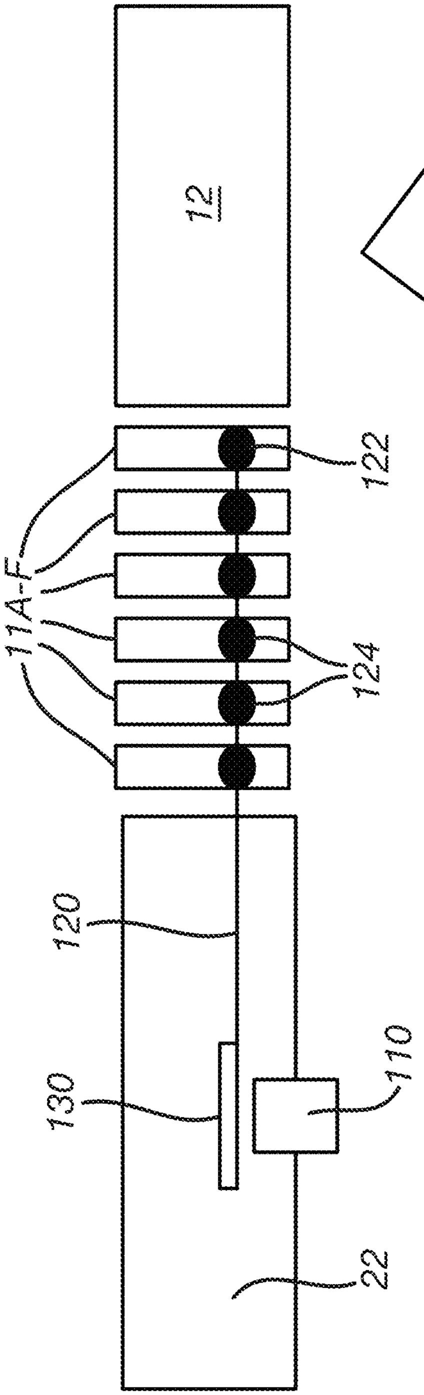
FIGS. 9A and 9B depict an example of a movement of the component of FIG. 8.
Figure 9B:
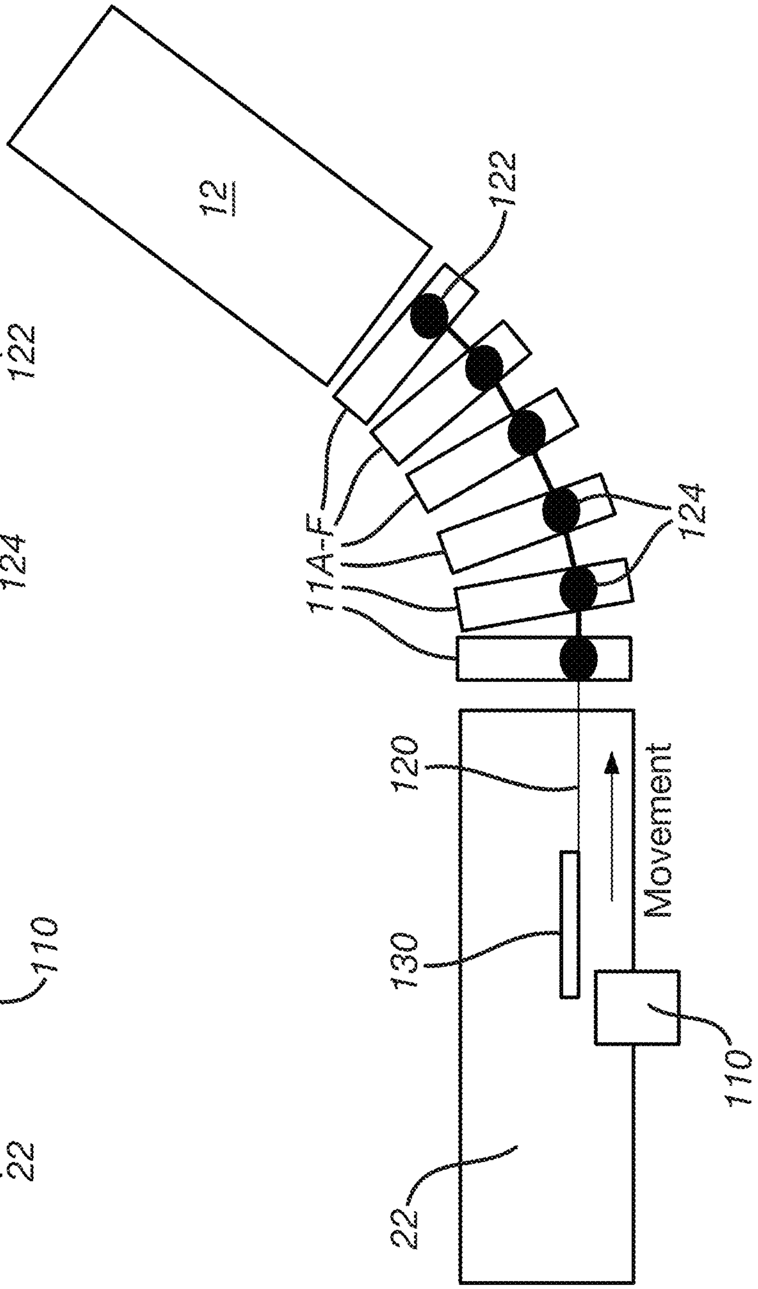

FIGS. 9A and 9B depict an example of the movement of the mechanical connector 120. FIG. 9A includes the shaft

22, the end effector 12, the mechanical connector 120 including a scale 130, an articulation joint 11 having six rib or disc members 11*a-f*, and six guides 124 including a connection 122 to a first rib member 11*a* of the articulation joint 11 where the mechanical connector 120 is anchored, attached, or connected. There may be fewer or more ribs or disc members 11*a-f* in the articulation joint 11. Additional guides or channels may be used. Other components such as the connections between the other rib members of the articulation joint 11 are not shown. In FIG. 9A, the end effector 12 may be positioned in a "ground" position. The ground position may be considered a starting position where the end effector 12 and rib members 11*a-f* of the articulation joint 11 are oriented in line with the shaft 22. The sensor 110 is configured to read the scale 130 and determine whether the device is at a ground position. In an embodiment, the ground position and its relationship with the scale 130 may be defined during a calibration process. The device may identify when the end effector 12 is directly aligned with the shaft 22. The sensor 110 measurement of the scale 130 at this point may be used as a ground reference point. If the sensor 110 reading of the scale 130 does not match the ground reference point, then the end effector 12 is not in a ground position. Minor adjustments may be made prior to each use to make sure the end effector 12 starts at the ground position. Due to various forces on the end effector 12 such as the insertion into a patient or the closing of the jaw, a ground position may not be directly orientated in line with the shaft 22 after a single use of the device. In another example, the end effector 12 may be articulated to perform a procedure and then removed from the patient body. After removal, the data from the sensor 110 may indicate that the end effector 12 is not at a ground position. Due to the articulation, the end effector 12 may not return to the factory ground position, but rather still be articulated by one or more degrees. The end effector 12 may be articulated or adjusted by an operator or robot to return to the ground position. Alternatively, if the articulation is known, the end effector 12 may be used again starting from this alternative starting position.

As described, during a procedure, the end effector 12 may be articulated in different directions. Using the articulation joint 11 the end effector 12 may be articulated, for example up to 65 degrees, up to 110 degrees, or more in relation to the shaft 22. FIG. 9B depicts an example where the end effector 12 has been articulated approximately 45 degrees in one direction. When the end effector 12 is articulated, the distance between the rib members 11*a-f* of the articulation joint 11 increases or decreases. The result is that since the mechanical connector 120 is fixed to one of the rib members 11*a-f* of the articulation joint 11 at the distal end of the mechanical connector 120, the mechanical connector 120 moves when the end effector 12 is articulated. The movement of the distal end of the mechanical connector 120 pulls on the proximal end that includes the scale 130. The movement of the scale 130 (e.g., the current position of the scale 130 vs a previous reading) is measured by the sensor 110. A device controller 170 inputs the sensor data and determines the pose, orientation, position, and/or displacement of the end effector 12. Multiple mechanical connectors 120 and sensors 110 may be used with different components (or located on different locations of a single component) in order to provide multiple measurements that may be used by the device controller 170.

Figure 10:
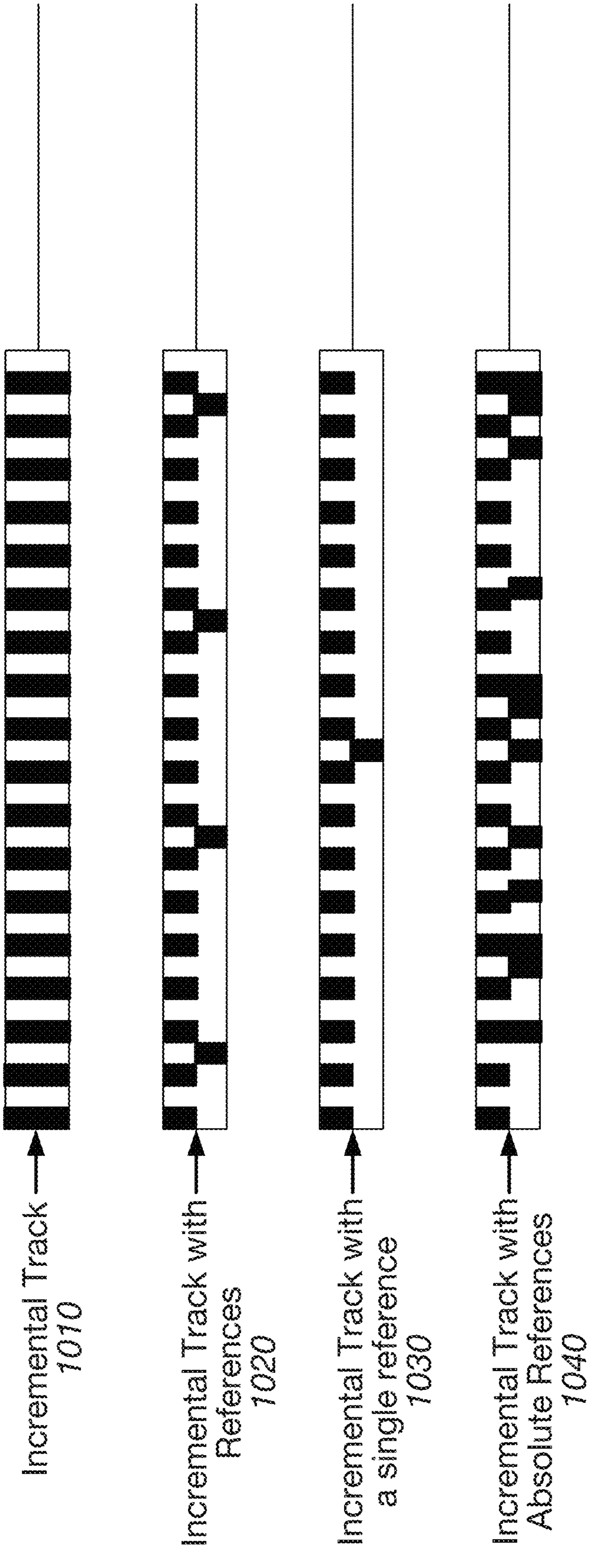
FIG. 10 depicts examples of scales of the system of FIG. 8.

As mentioned above, the mechanical connector 120 includes a scale 130 (also referred to as a coded strip) at or towards the proximal end of the mechanical connector 120. The scale 130 may include one or more tracks that include at least one detectable mark or reference that the sensor 110 may read or detect in order to determine the position or movement of the scale 130. In an example, the scale 130 may include optical, magnetic, or mechanical marks on, or embedded in, its surface that help the sensor 110 to determine its current position. The marks/references may be magnetic, optical, or otherwise detectable by the sensor 110. FIG. 10 depicts an example of different scales 130. Scales may include one or more tracks. FIG. 10 includes a scale with just an incremental track 1010, a scale with an incremental track with a second track including references 1020, a scale with an incremental track with a single reference 1030, and a scale with an incremental track with a second track with absolute references 1040. The marks/references are depicted as examples and may be more complex or detailed in order to provide additional distinctions. The incremental track 1010 includes a single track with regularly spaced referenced marks. The incremental track with references 1020 includes an additional track that includes reference marks. The incremental track with a single reference 1030 includes an additional track that includes a single reference such as a ground reference. The incremental track with absolute references 1040 includes an additional track that provides various unique references. Each of the marks/references may be offset from each other by a certain distance (such as an incremental track) or the marks may be offset by varying distances (such as in an absolute track). One or more tracks may be used depending on the sensor 110. In one embodiment, more than one sensors 110 may be used to read different tracks on the scale 130. In an embodiment, the scale 130 is or includes a magnetic code, an optical code, or a mechanical code that provides the marks/references. The scale 130 is read or detected by a sensor 110 that is located in the shaft 22 of the device. The sensor 110 is configured to read the scale 130 as the scale 130 moves back and forth due to movement of the mechanical component.

In an embodiment, the sensor 110 is a linear encoder. As the scale 130 slides past a fixed encoder read head, the linear encoder reads the scale 130 and determines the amount the scale 130 moved. The scale 130 moves back and forth along a long axis (linearly) of the shaft 22. The sensor 110 may be able to detect a speed, a distance, a direction, and/or a displacement of the scale 130. In an embodiment, the sensor 110 may be an absolute linear encoder or an incremental linear encoder. As described above, FIG. 10 depicts various scales including incremental tracks and absolute tracks. An absolute linear encoder may accurately determine a current position by reading the unique reference marks. When the sensor 110 reads a mark, the resulting signal or data indicates a unique position on the scale 130 and thus its absolute position. An incremental linear encoder detects a position offset relative to specific points. The marks on the scale 130 may be identical to each other. With an incremental encoder, the sensor 110 is configured to determine a relative distance moved but not an absolute position. When the sensor 110 is turned off, the latest location status information disappears. Additional special markings or labels such as reference or starting marks may be used. In one example, origin or zero point markings may be used. If the device controller 170 can identify a reference or starting location and a distance moved from that location, the device controller 170 may be able to determine a current position of the end effector 12 by comparing the two. In the example of the incremental track with a single reference 1030, the single reference may indicate a ground or factory calibrated position. If the scale 130 and sensor 110 are not lined up so that the sensor 110 reads the ground reference, the end effector 12 is thus not at a "ground" position.

In an embodiment, the sensor 110 is a magnetic linear encoder that uses a magnetic reader head for analyzing changes in magnetic fluxes for displacement analysis. In this embodiment, the scale 130 includes a set of poles (north and south) that are magnetically coded. The poles are arranged in a specific way depending on the type of scale 130 (incremental or absolute). When the sensor 110 passes over each pole on the magnetic scale 130, the sensor 110 reads current changes in the magnetic fields. For a magnetic linear encoder, the sensor 110 may be a Hall sensor.

In an embodiment, the sensor 110 is an optical linear encoder that uses light beams or lasers as a signal. In this embodiment, the scale 130 includes transparent (clear) or opaque areas as marks. Using an optical linear encoder may provide linear measurements with the greatest accuracy and high resolution but has certain drawbacks. Dust or other particles in a gap between the measuring surface and sensor 110 as well as mechanical shocks and vibrations may significantly affect the accuracy. The linear encoder may include protection to prevent contamination from dust, vibrations, and other conditions. The sensor 110 may include infrared LEDs, visible LEDs, miniature lightbulbs, and/or laser diodes to generate the signal.

In an embodiment, the sensor 110 is an optical image sensor. In this embodiment, the optical image sensor takes pictures of the scale 130 as the scale 130 moves. The device controller 170 compares the images for displacement. As with the optimal linear encoder, the sensor 110 may include protection to prevent contamination from dust, vibrations, and other conditions.

The scale 130 may include or provide an index or reference mark providing a datum position along the scale 130 for use at power-up or following a loss of power. The incremental track with a single reference 1030 as depicted in FIG. 10 is an example of a such a reference mark. The index or datum allows the system to identify a position of the scale 130 within one, unique period of the scale 130. The reference mark may include, for example, a single feature on the scale 130, an autocorrelator pattern (for example a Barker code) or a chirp pattern. In addition, distance coded reference marks (DCRM) may be placed onto the scale 130 in a unique pattern allowing a minimal movement (typically moving past two reference marks) to define the read head's position. Multiple, equally spaced reference marks may also be placed onto the scale 130 such that during installation or calibration, the desired mark may either be selected or unwanted marks deselected.

Signals from the sensor 110 are transmitted to the device controller 170 and/or another computing device. The device controller 170 includes a processor and a memory storing program instructions, which when executed by the processor, causes the processor to perform one or more aspects of the process. The processor computes at least one transfer function that provides a translation of an electrical signal produced by the sensor 110 and the movement. The at least one transfer function may be a first-order equation or use a lookup-table for example. The device controller 170 may be configured to analyze the signals from the sensor 110 and determine at least one of a position, pose, displacement, or orientation of a component of interest and/or the end effector 12.

The device controller 170 may be configured to use a predetermined algorithm to convert the sensor's 110 reading to a useful value, such as a current yaw-angle. In an example with multiple mechanical connectors 120 the yaw and pitch may be measured separately by two different sensors, and these encoder-count readings are converted to an angle indicating the actual angular position. For an encoder, the device controller 170 may be configured to convert the number of counts from zero at the yaw sensor to an angular value of yaw. Various conversions might be used. For example, a simple linear equation (yaw angle=m(counts)+b) may be used or a more sophisticated function—such as piecewise-linear fit, a polynomial fit, or a lookup-table may be used.

The device controller 170 may be configured to display a value, such as a current yaw-angle, to the user. Alternatively, or additional, the device controller 170 may be configured to use the value internally. For instance, the device controller 170 may feed the value back to the control system to correct a position of the tip to the desired position.

While being able to determine the position, pose, displacement, stability, or orientation of a single component of interest is useful, a better understanding may be provided by multiple sensors 110 determining the displacement of multiple components of interest.

Figure 11:
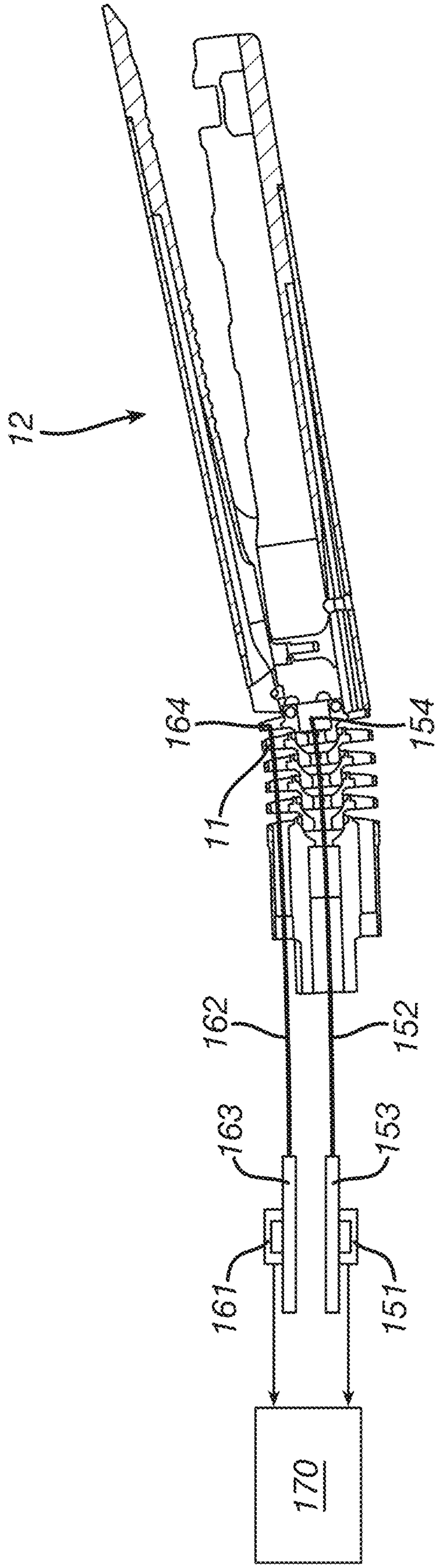
FIG. 11 depicts a side view of a system with two sensors for detecting movement of a component of an end effector.

FIG. 11 depicts an example of an embodiment where two sensors 151, 161 are used to measure a pitch and a yaw of the end effector 12. The system of FIG. 11 includes a first sensor 151 and a first mechanical connector 152 that is attached to a first position 154 on an articulation joint 11. As depicted, the first position 154 on the articulation joint 11 is a position on the articulation joint 11 closest to the end effector 12. Another position on the articulation joint 11 may be used. The system of FIG. 11 also includes a second sensor 161 and a second mechanical connector 162 that is attached to a second position 164 on the articulation joint 11. The connectors 152, 162 are attached to the same rib or disc member of the articulation joint 11 in FIG. 11, but may be attached to different components. Each mechanical connector 152, 162 includes its own scale 153, 163 that is read by the respective sensors 151, 161. When the end effector 12 is articulated or moved, the articulation joint 11 may move. The two positions (first position 154 and second position 164) may move different distances depending on the type of movement of the end effector 12. The movement of each of the positions 154, 164 is translated to movement of the respective scales 153, 163 by the mechanical connectors 152, 162. The two sensors 151, 161 read their respective scales 153, 163 and transmit a signal to the device controller 170. The signals may be related to the yaw or pitch movement of the end effector 12. For example, the first sensor 151 and respective first mechanical connector 152 and first scale 153 may read a yaw movement of the end effector 12 while the second sensor 161 and respective second mechanical connector 162 and second scale 163 may read a pitch movement of the end effector 12. The device controller 170 analyzes the signals to determine a position, pose, displacement, or orientation of the end effector 12.

Figure 12:
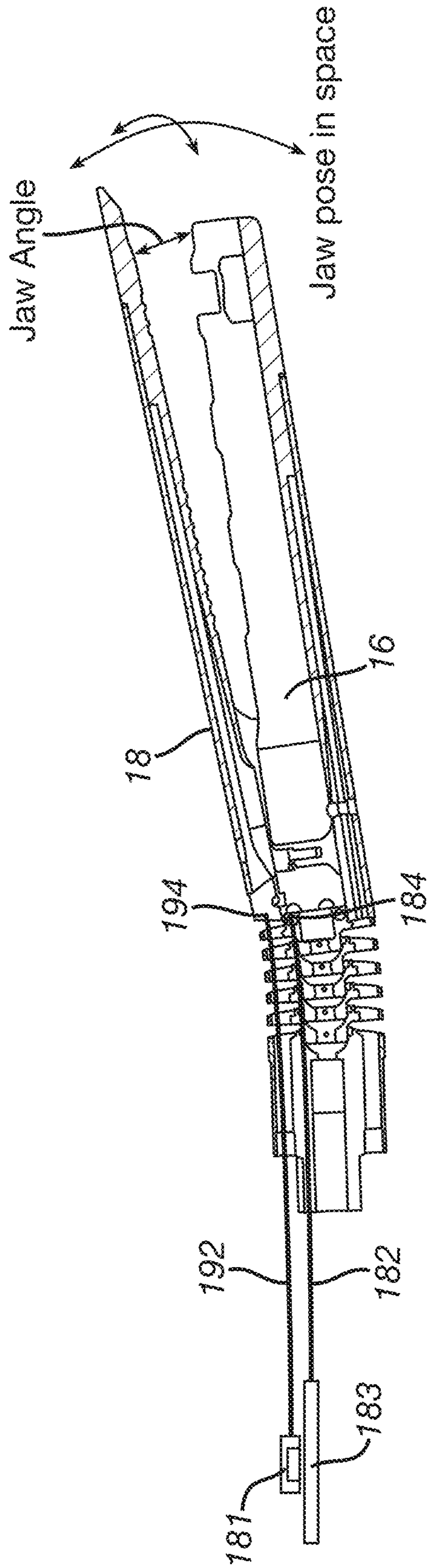
FIG. 12 depicts a side view of a system with one sensor for detecting relative movement of components of an end effector.

FIG. 12 depicts another example of an embodiment where a single sensor is used with two mechanical connectors. The system of FIG. 12 includes a single sensor 181 that is attached to a first mechanical connector 192 that is attached at a point 194 to a first mechanical component, here the upper jaw 18. The first mechanical connector 192 does not include a scale 130 but rather is attached to the sensor 181 at a distal end of the sensor 181 (i.e., the proximal end of the first mechanical connector 192 is attached to the distal end of the sensor 181). The system of FIG. 12 further includes a second mechanical connector 182 that is attached at a point 184 to a second mechanical component, here the lower jaw 16. The second mechanical connector 182 includes a scale 183 that is read by the sensor 181. In operation, the system measures the differential movement of the two mechanical components 16, 18. For example, if the first mechanical component is the pivotable anvil jaw 18 (upper jaw member) and the second mechanical component is the lower jaw 16, then the sensor 181 measures the differential movement of the pivotable anvil jaw 18 and the lower jaw 16. If the pivotable anvil jaw 18 moves and the lower jaw 16 does not, the sensor 181 will detect movement. If the pivotable anvil jaw 18 moves and the lower jaw 16 moves the same amount, then the sensor 181 will not detect any movement as the sensor would read the same location on the scale 183. This type of differential analysis may be used in the example of a combination where there is no differential movement detected when the entire end effector 12 is articulated but there is differential movement when the jaw angle changes due to the pivotable anvil jaw 18 moving and the lower jaw 16 not moving. If there is movement detected, the jaw angle may be determined to have changed. If the only movement is a change in the jaw pose, then there may be no movement detected as the two components (pivotable anvil jaw 18, lower jaw 16) move in unison. If the jaw pose and the jaw angle change, movement will be detected.

The embodiments of FIG. 11 and FIG. 12 may be combined such that the system of FIG. 12 may also be used to measure one aspect of the movement of a component of interest of the end effector 12. Another fixed sensor 110 may be used to measure the movement of one of the mechanical connectors of FIG. 12. The system of FIG. 12 may thus be used with the additional sensor to measure one aspect of the movement, e.g., a pitch or yaw of the end effector 12, while another sensor such as a sensor 161 in FIG. 11 may be used to measure another aspect of the movement, for example the other of the pitch or yaw of the end effector 12.

Figure 13:
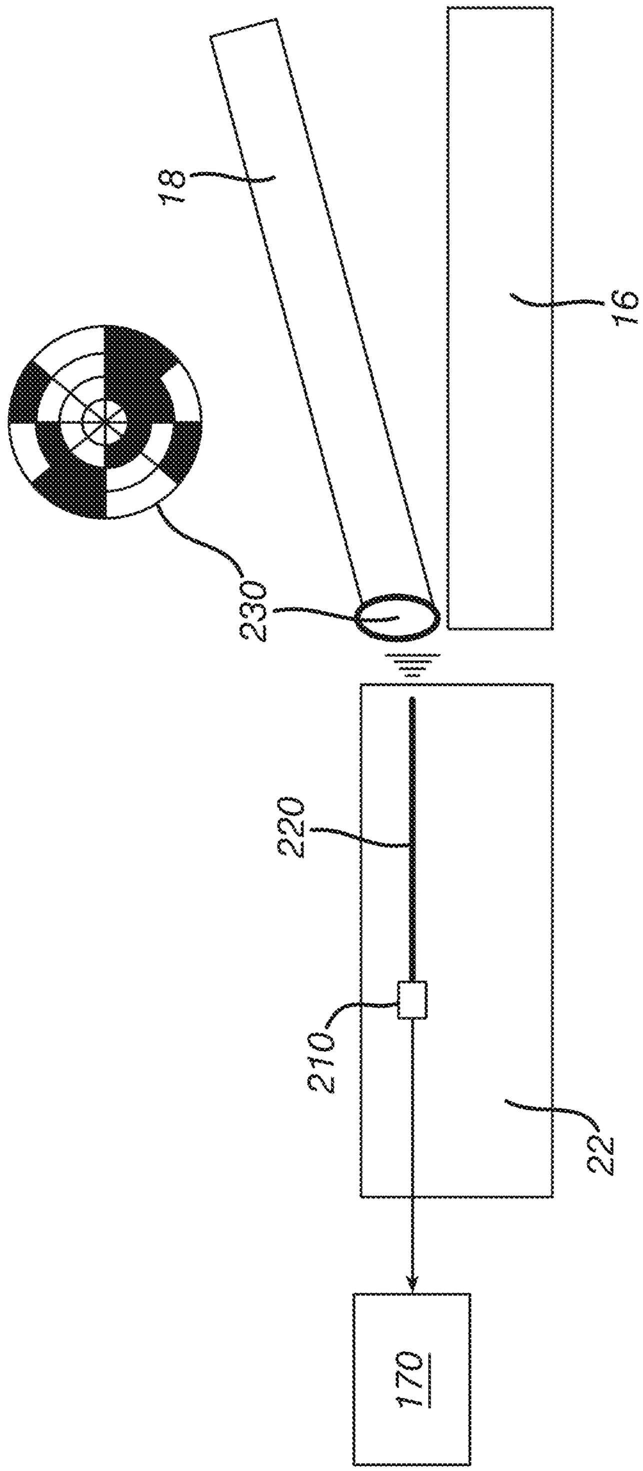
FIG. 13 depicts a side view of a fiber optic sensor for detecting movement of a component of an end effector.

FIG. 13 depicts another embodiment that uses a fiber optic wire 220 instead of a mechanical connector. The fiber optic wire 220 runs from a sensor 210 located in the shaft 22 to a location near or at a part of interest, for example, the pivotable anvil jaw 18. In this example, the fiber optic wire 220 runs along a longitudinal axis of the device shaft 22, which reads an encoder pattern 230 etched on a back surface of the pivotable anvil jaw 18 to detect the position/pose of the pivotable anvil jaw 18. The pattern 230 is visible by the signals emitted from the fiber optic wire 220 when looking at the proximal end of the pivotable anvil jaw 18 axially to the shaft 22. When the pivotable anvil jaw 18 moves, the encoder pattern 230 moves which is detected by the signals from the fiber optic wire 220. Additional sensors (additional rotary encoders or hall effect sensors) in the shaft 22 may be provided to detect the location of the closure handle to establish and input/output relationship.

During application, it will be appreciated that as a user urges the instrument into a surgical region, it may be desirable to approach the tissue to be clamped, stapled, or cut, from a particular angle. For instance, once the end effector 12 of instrument is inserted through a trocar, thoracotomy, or other passageway for entering a surgical area, the tissue that the user wishes to target may be positioned out of reach or at an askew angle in relation to end effector 12 that is aligned with the shaft 22. Thus, it may be desirable for portions of instrument, such as the end effector 12, to articulate such that the user can position the pivotable anvil jaw 18 and the lower jaw 16 of the end effector 12 to squarely or perpendicularly clamp against a vessel or other tissue.

When the end effector 12 or portions thereof are articulated or moved, the movement is translated back to sensors in the shaft 22 by the mechanical connector. The pose, orientation, alignment, and/or position of the end effector 12 may be determined by the device controller 170 by analyzing signals from the sensor 110 that is located in the shaft 22 and that is configured to read a scale 130 at the proximal end of the mechanical connector 120. In another use, the sensor 110 may read the scale 130 to determine if the end effector 12 is at a ground position.

In an alternative embodiment, the mechanical connector 120 may be combined with a load-bearing member (i.e., using an articulation cable to move the encoder/sensor member). In this case, a transfer-function may ignore or compensate for friction/compliance of the mechanical connector 120 to the mechanical component.

VI. Examples of Combinations

The following examples/clauses relate to various non-exhaustive ways in which the teachings herein may be combined or applied. It should be understood that the following examples/clauses are not intended to restrict the coverage of any claims that may be presented at any time in this application or in subsequent filings of this application. No disclaimer is intended. The following examples/clauses are being provided for nothing more than merely illustrative purposes. It is contemplated that the various teachings herein may be arranged and applied in numerous other ways. It is also contemplated that some variations may omit certain features referred to in the below examples/clauses. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Illustrative Embodiment 1. A system for determining mechanical displacement in an endoscopic device comprising a shaft connected to an end effector, the system comprising:

- a first component located in the end effector;
- a first mechanical connector extending through the shaft and connected at a distal end of the first mechanical connector to the first component, wherein movement of the first component imparts movement in at least a proximal end of the first mechanical connector; and
- a first sensor located in the shaft and configured to detect movement of the first mechanical connector and generate a signal indicative thereof, the generated signal being further indicative of the movement of the first component.

Illustrative Embodiment 2. The system of Illustrative Embodiment 1, further comprising:

- a device controller configured to determine a pose of the first component based on the detected movement by the first sensor.

Illustrative Embodiment 3. The system of Illustrative Embodiment 1, wherein the first sensor comprises a linear encoder.

Illustrative Embodiment 4. The system of Illustrative Embodiment 3, wherein the linear encoder is a magnetic linear encoder, wherein the first mechanical connector includes a magnetically encoded scale that is read by the magnetic linear encoder.

Illustrative Embodiment 5. The system of Illustrative Embodiment 3, wherein the linear encoder is an optical encoder, wherein the first mechanical connector includes an optically encoded scale that is read by the optical encoder.

Illustrative Embodiment 6. The system of Illustrative Embodiment 1, wherein the first mechanical connector is connected to the end effector at a first location to measure a yaw motion of the end effector or a second location of the end effector to measure a pitch motion of the end effector.

Illustrative Embodiment 7. The system of Illustrative Embodiment 6, wherein the first mechanical connector is connected at the first location, the system further comprising:

- a second mechanical connector extending through the shaft and connected at a distal end of the second mechanical connector to the first component at the second location, wherein movement of the first component imparts movement in the second mechanical connector; and
- a second sensor located in the shaft and configured to detect movement of the second mechanical connector and generate a signal indicative thereof, the generated signal being further indicative of the pitch motion of the first component.

Illustrative Embodiment 8. The system of Illustrative Embodiment 1, wherein the first component comprises an upper jaw of the end effector.

Illustrative Embodiment 9. The system of Illustrative Embodiment 1, wherein the first component comprises a lower jaw of the end effector.

Illustrative Embodiment 10. The system of Illustrative Embodiment 1, wherein the first mechanical connector comprises a steel wire or a Nitinol filament.

Illustrative Embodiment 11. The system of Illustrative Embodiment 1, wherein the first sensor is configured to detect movement of the first mechanical connector by reading a scale located at a proximal end of the first mechanical connector.

Illustrative Embodiment 12. The system of Illustrative Embodiment 11, wherein the scale includes a plurality of incremental markings and at least one reference marking.

Illustrative Embodiment 13. A system for determining a pose of an end effector of an endoscopic device comprising a shaft connected to the end effector, the system comprising:

- a component located in the end effector;
- a first mechanical connector attached at a distal end of the first mechanical connector to the component at a first location on the component, the first mechanical connector including a first scale at a proximal end of the first mechanical connector;
- a second mechanical connector attached at a distal end of the second mechanical connector to the component at a second location on the component, the second mechanical connector including a second scale at a proximal end of the second mechanical connector;
- a first sensor located in the shaft, the first sensor configured to read the first scale and generate a first signal;
- a second sensor located in the shaft, the second sensor configured to read the second scale and generate a second signal; and
- a device controller configured to determine a pose of the component based on the first signal and the second signal;
- wherein movement of the component causes the first mechanical connector, the second mechanical connector, or the first mechanical connector and the second mechanical connector to move along an axis of the shaft.

Illustrative Embodiment 14. The system of Illustrative Embodiment 13, wherein the device controller is configured to determine if the end effector is at a home position based on the first signal and the second signal.

Illustrative Embodiment 15. The system of Illustrative Embodiment 13, wherein each of the first sensor and the second sensor comprises a magnetic encoder or an optical encoder.

Illustrative Embodiment 16. The system of Illustrative Embodiment 13, wherein the component comprises an upper jaw or lower jaw of the end effector.

Illustrative Embodiment 17. The system of Illustrative Embodiment 13, wherein the component comprises an articulation joint.

Illustrative Embodiment 18. The system of Illustrative Embodiment 13, wherein the first mechanical connector and the second mechanical connector comprise steel wires or Nitinol filaments.

Illustrative Embodiment 19. A system for determining displacement of a surgical stapler comprising a shaft connected to an end effector, the system comprising:

- a first movable stapler component located in the end effector;
- a second movable stapler component located in the end effector;
- a first mechanical connector comprising a distal end and a proximal end, the distal end of the first mechanical connector being attached to the first movable stapler component, the proximal end of the first mechanical connector including a scale, wherein movement of the first movable stapler component causes the first mechanical connector and the scale to move along a long axis of the shaft;
- a second mechanical connector comprising a distal end and a proximal end, the distal end of the second mechanical connector being attached to the second movable stapler component, the proximal end of the second mechanical connector being attached to a sensor, wherein movement of the second movable stapler component causes the second mechanical connector and the sensor to move along the long axis of the shaft, wherein the sensor is configured to read the scale of the first mechanical connector and generate a signal; and
- a device controller configured to determine a pose of the first movable stapler component in relation to the second movable stapler component based on the signal.

Illustrative Embodiment 20. The system of Illustrative Embodiment 19, wherein the first movable stapler component is a lower jaw of the end effector and the second movable stapler component is an upper jaw of the end effector.

VII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. App. No. 63/467,622, entitled "Surgical Stapler Cartridge Having Intermediate Raised Tissue Engagement Protrusions," filed on May 19, 2023; U.S. Pat. App. No. 63/467,623, entitled "Surgical Stapler Cartridge Having Tissue Engagement Protrusions with Enlarged Engagement Surface," filed on May 19, 2023; U.S. Pat. App. No. 63/467,648, entitled "Surgical Stapler Cartridge Having Raised Surface to Promote Buttress Adhesion," filed on May 19, 2023; U.S. Pat. App. No. 63/467,469, entitled "Surgical Stapler Cartridge Having Cartridge Retention Features," filed on May 19, 2023; U.S. Pat. App. No. 63/459,739, entitled "Surgical Stapler Anvil Having Staple Forming Pockets with Laterally Varying Orientations," filed on May 19, 2023; U.S. Pat. App. No. 63/467,656, entitled "Surgical Stapler With Discretely Positionable Distal Tip," filed on May 19, 2023; and/or U.S. Pat. App. No. 63/467,615, entitled "Incompatible Staple Cartridge Use Prevention Features for Surgical Stapler," filed on May 19, 2023.

Additionally, any one or more of the teachings herein may be combined with any one or more of the teachings disclosed in U.S. Pat. App. No. 63/459,739, entitled "Surgical Stapler Anvil Having Staple Forming Pockets with Laterally Varying Orientations," filed on Apr. 17, 2023. The disclosure of each of these U.S. patent applications is incorporated by reference herein in its entirety.

Additionally, any one or more of the teachings herein may be combined with any one or more of the teachings disclosed in U.S. Pat. No. 11,304,697, entitled "Surgical Stapler with Deflectable Distal Tip," issued Apr. 19, 2022, the disclosure of which is incorporated by reference herein, in its entirety; U.S. Pat. No. 11,317,912, entitled "Surgical Stapler with Rotatable Distal Tip," issued May 3, 2022, the disclosure of which is incorporated by reference herein, in its entirety; and/or U.S. Pat. No. 11,439,391, entitled "Surgical Stapler with Toggling Distal Tip," issued Sep. 13, 2022, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A system for determining mechanical displacement in an endoscopic device comprising a shaft connected to an end effector, the system comprising:

- a first component located in the end effector;
- a first mechanical connector extending through the shaft and connected at a distal end of the first mechanical connector to the first component, wherein movement of the first component imparts movement in at least a proximal end of the first mechanical connector, wherein the first mechanical connector is connected to the end effector at a first location to measure a yaw motion of the end effector;
- a second mechanical connector extending through the shaft and connected at a distal end of the second mechanical connector to the first component at a second location of the end effector to measure a pitch motion of the end effector, wherein movement of the first component imparts movement in the second mechanical connector;
- a first sensor located in the shaft and configured to detect movement of the first mechanical connector and generate a signal indicative thereof, the generated signal being further indicative of the movement of the first component; and a second sensor located in the shaft and configured to detect movement of the second mechanical connector and generate a signal indicative thereof, the generated signal being further indicative of the pitch motion of the first component.

2. The system of claim 1, further comprising:

a device controller configured to determine a pose of the first component based on the detected movement by the first sensor.

3. The system of claim 1, wherein the first sensor comprises a linear encoder.

4. The system of claim 3, wherein the linear encoder is a magnetic linear encoder, wherein the first mechanical connector includes a magnetically encoded scale that is read by the magnetic linear encoder.

5. The system of claim 3, wherein the linear encoder is an optical encoder, wherein the first mechanical connector includes an optically encoded scale that is read by the optical encoder.

6. The system of claim 1, wherein the first component comprises an upper jaw of the end effector.

7. The system of claim 1, wherein the first component comprises a lower jaw of the end effector.

8. The system of claim 1, wherein the first mechanical connector comprises a steel wire or a nitinol filament.

9. The system of claim 1, wherein the first sensor is configured to detect movement of the first mechanical connector by reading a scale located at a proximal end of the first mechanical connector.

10. The system of claim 9, wherein the scale includes a plurality of incremental markings and at least one reference marking.

11. A system for determining a pose of an end effector of an endoscopic device comprising a shaft connected to the end effector, the system comprising:

a component located in the end effector;

a first mechanical connector extending through the shaft and attached at a distal end of the first mechanical connector to the component at a first location on the component, the first mechanical connector including a first scale at a proximal end of the first mechanical connector;

a second mechanical connector extending through the shaft and attached at a distal end of the second mechanical connector to the component at a second location on the component, the second mechanical connector including a second scale at a proximal end of the second mechanical connector;

a first sensor located in the shaft, the first sensor configured to read the first scale and generate a first signal that is indicative of movement of the first mechanical connector and a yaw motion of the component;

a second sensor located in the shaft, the second sensor configured to read the second scale and generate a second signal that is indicative of movement of the second mechanical connector and a pitch motion of the component; and a device controller configured to determine a pose of the component based on the first signal and the second signal;

wherein movement of the component causes the first mechanical connector, the second mechanical connector, or the first mechanical connector and the second mechanical connector to move along an axis of the shaft.

12. The system of claim 11, wherein the device controller is configured to determine if the end effector is at a home position based on the first signal and the second signal.

13. The system of claim 11, wherein each of the first sensor and the second sensor comprises a magnetic encoder or an optical encoder.

14. The system of claim 11, wherein the component comprises an upper jaw or lower jaw of the end effector.

15. The system of claim 11, wherein the component comprises an articulation joint.

16. The system of claim 11, wherein the first mechanical connector and the second mechanical connector comprise steel wires or nitinol filaments.

* * * * *